(12) United States Patent
Nakamura et al.

(10) Patent No.: US 9,173,556 B2
(45) Date of Patent: Nov. 3, 2015

(54) EYE MEASUREMENT APPARATUS

(75) Inventors: Kenji Nakamura, Toyohashi (JP);
Mitsuhiro Gono, Toyokawa (JP)

(73) Assignee: NIDEK CO., LTD., Aichi (JP)

( * ) Notice: Subject to any disclaimer, the term of this patent is extended or adjusted under 35 U.S.C. 154(b) by 927 days.

(21) Appl. No.: 13/334,944

(22) Filed: Dec. 22, 2011

(65) Prior Publication Data

US 2012/0162606 A1    Jun. 28, 2012

(30) Foreign Application Priority Data

Dec. 27, 2010   (JP) .................... 2010-291187

(51) Int. Cl.
*A61B 3/10* (2006.01)
*A61B 3/00* (2006.01)
*A61B 3/032* (2006.01)
*A61B 3/036* (2006.01)

(52) U.S. Cl.
CPC .............. *A61B 3/0008* (2013.01); *A61B 3/032* (2013.01); *A61B 3/036* (2013.01)

(58) Field of Classification Search
CPC ............ A61B 3/14; A61B 3/12; A61B 3/103; A61B 3/1015; A61B 3/1225; A61B 3/0008; A61B 3/032; A61B 3/036

USPC .......... 351/200, 205, 206, 210, 221, 222, 246
See application file for complete search history.

(56) References Cited

U.S. PATENT DOCUMENTS

2004/0004694 A1* 1/2004 Sugino et al. ................ 351/206
2007/0128174 A1* 6/2007 Kleinsek et al. ............ 424/93.7

FOREIGN PATENT DOCUMENTS

JP           7016205 A      1/1995

* cited by examiner

*Primary Examiner* — James Greece
(74) *Attorney, Agent, or Firm* — Rankin, Hill & Clark LLP

(57) ABSTRACT

An eye measurement apparatus includes: a subjective measurement optical system configured to subjectively measure an examinee's eye, the subjective measurement optical system including: a chart to be presented to the examinee's eye; and a glare light source for irradiating the examinee's eye with a glare light; and a control part configured to determine presence or absence of opacity in a light transmitting part of the examinee's eye and, when the presence of opacity is determined, to allow display of necessity for a glare test which is a subjective measurement to be performed in a state that the examinee's eye is irradiated with the glare light.

19 Claims, 3 Drawing Sheets

EYE MEASUREMENT APPARATUS

CROSS-REFERENCE TO RELATED APPLICATION

This application claims priority from Japanese Patent Application No. 2010-291187 filed with the Japan Patent Office on Dec. 27, 2010, the entire content of which is hereby incorporated by reference.

BACKGROUND

1. Technical Field

The present disclosure relates to an eye measurement apparatus for measuring an examinee's eye.

2. Related Art

An apparatus such as an auto-refractometer has been known to objectively measure an eye refractive power of an examinee's eye by projecting a measurement light flux to a fundus of the eye and receiving the light reflected thereby.

There is an eye refractive power measurement apparatus including an optical system for glare test. Such an apparatus is disclosed in JP-A-7-16205.

SUMMARY

An eye measurement apparatus according to a first aspect of the present disclosure includes: a subjective measurement optical system configured to subjectively measure an examinee's eye, the subjective measurement optical system including: a chart to be presented to the examinee's eye; and a glare light source for irradiating the examinee's eye with a glare light; and a control part configured to determine presence or absence of opacity in a light transmitting part of the examinee's eye and, when the presence of opacity is determined, to allow display of necessity for a glare test which is a subjective measurement to be performed in a state that the examinee's eye is irradiated with the glare light.

An eye measurement apparatus according to a second aspect of the present disclosure includes: a subjective measurement optical system configured to subjectively measure an examinee's eye, the subjective measurement optical system including: a chart to be presented to the examinee's eye; and a glare light source for irradiating the examinee's eye with a glare light; and a control part configured to determine presence or absence of opacity in a light transmitting part of the examinee's eye and, when the presence of opacity is determined, to control the subjective measurement optical system to execute a glare test which is a subjective measurement to be performed in a state that the examinee's eye is irradiated with the glare light.

DETAILED DESCRIPTION

Figure 1:
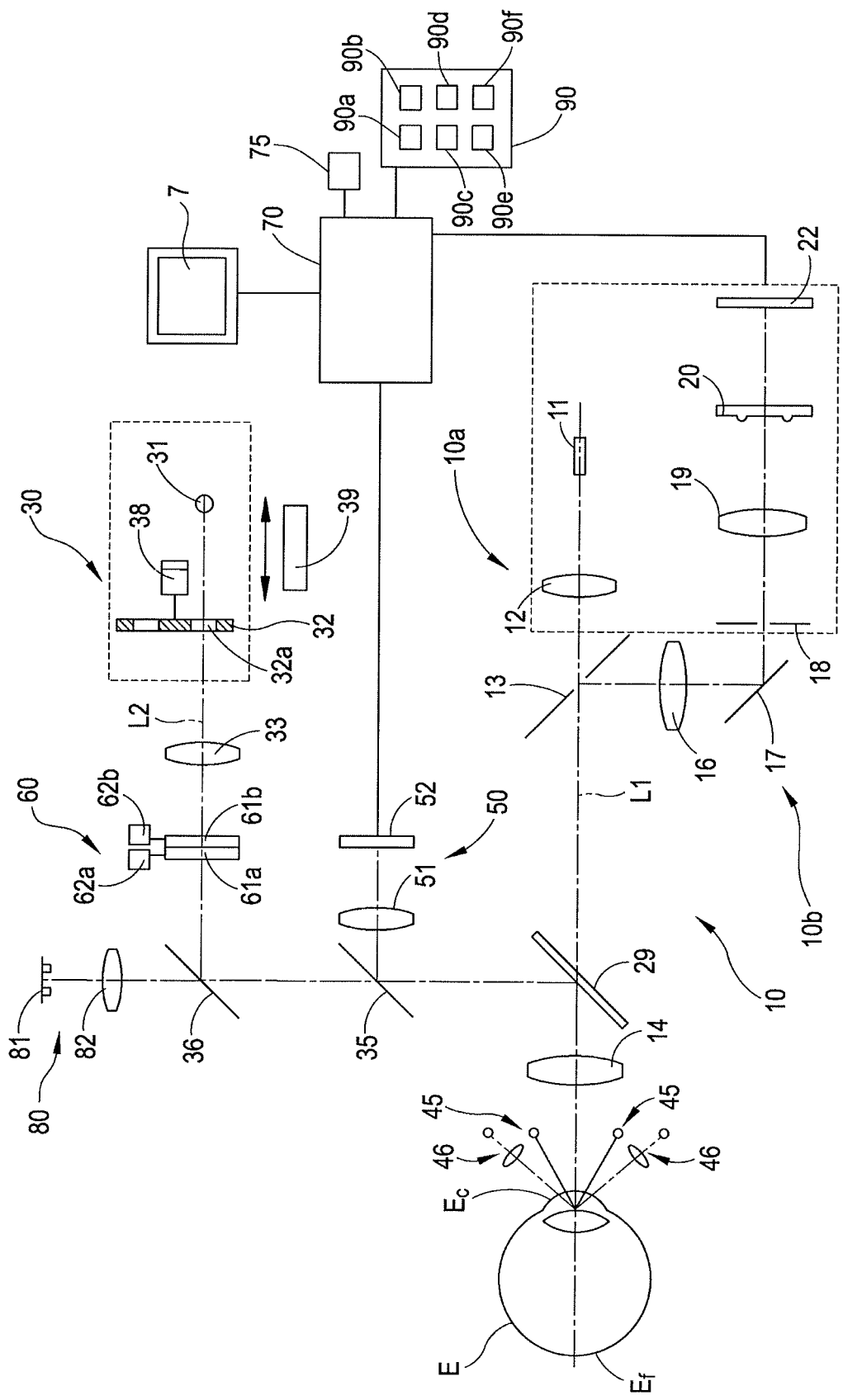
FIG. 1 is a schematic configuration diagram illustrating an optical system and a control system of an eye measurement apparatus according to an embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Examiners determine whether each of examinees needs a glare test based on experiences thereof. However, inexperienced examiners may have difficulty in determining the necessity for glare test. If the glare test is performed on every examinee, a time required for a series of tests including an objective test and a glare test is prolonged, causing an increase in burdens on an examinee and an examiner.

One aspect of the present disclosure is to provide an eye measurement apparatus capable of smoothly performing a glare test.

The eye measurement apparatus according to an embodiment may have the following configuration.

An eye measurement apparatus according to a first aspect of the present disclosure includes: a subjective measurement optical system configured to subjectively measure an examinee's eye, the subjective measurement optical system including: a chart to be presented to the examinee's eye; and a glare light source for irradiating the examinee's eye with a glare light; and a control part configured to determine presence or absence of opacity in a light transmitting part of the examinee's eye and, when the presence of opacity is determined, to allow display of necessity for a glare test which is a subjective measurement to be performed in a state that the examinee's eye is irradiated with the glare light.

An eye measurement apparatus according to a second aspect of the present disclosure includes: a subjective measurement optical system configured to subjectively measure an examinee's eye, the subjective measurement optical system including: a chart to be presented to the examinee's eye; and a glare light source for irradiating the examinee's eye with a glare light; and a control part configured to determine presence or absence of opacity in a light transmitting part of the examinee's eye and, when the presence of opacity is determined, to control the subjective measurement optical system to execute a glare test which is a subjective measurement to be performed in a state that the examinee's eye is irradiated with the glare light.

Such an eye measurement apparatus has high usability.

Now, a description is given of the eye measurement apparatus (or hereinafter called the apparatus) according to the embodiment with reference to the accompanying drawings. FIG. 1 is a schematic configuration diagram illustrating an optical system and a control system of the apparatus. Note that the optical system is installed inside a housing (not shown). The housing may be three-dimensionally moved with respect to an examinee's eye E by a known moving mechanism for alignment. The housing may be of hand-held type (handy-type).

A measurement optical system (objective measurement optical system, subjective measurement optical system) 10 includes a projecting optical system 10a and a light receiving optical system 10b. The projecting optical system (light projecting optical system) 10a projects a measurement chart having a spot shape to a fundus Ef of an examinee's eye E through a center portion of a pupil of the eye E. The light receiving optical system 10b receives a ring-shaped fundus reflection light that has been reflected by the fundus Ef and then passed through the periphery of the pupil. Accordingly, a two-dimensional imaging device captures a ring-shaped fundus reflection image.

The projecting optical system 10a includes a measurement light source I1, a relay lens 12, a hole mirror 13, and an objective lens 14. These members 11 through 14 are arranged on an optical axis L1 of the measurement optical system 10. The measurement light source I1 is positioned in optical conjugation with the fundus Ef of an emmetropic eye. The hole mirror 13 has an opening that is positioned in optical conjugation with a pupil of the eye E.

The light receiving optical system 10b shares the objective lens 14 and the hole mirror 13 with the projecting optical system 10a. The light receiving optical system 10b includes a relay lens 16 and a total reflection mirror 17 that are arranged on the optical axis L1 in a reflection direction of the hole mirror 13. Moreover, the light receiving optical system 10b includes a light receiving aperture 18, a collimator lens 19, a ring lens 20, and a two-dimensional imaging device (light receiving device) 22 including an area charge coupled device (CCD). These members 18, 19, 20, and 22 are arranged on the optical axis L1 in a reflection direction of the total reflection mirror 17. The light receiving aperture 18 and the imaging device 22 have optically conjugate positional relations with the fundus Ef. The ring lens 20 includes a lens portion formed in a ring shape, and a light shielding portion that serves as an area other than the lens portion and is coated with a light shielding. The ring lens 20 has an optically conjugate positional relation with the pupil of the eye E. An output from the imaging device 22 is input into a calculation control part 70 (hereinafter called control part 70).

Although the measurement optical system 10 has been described, it is not limited thereto. The measurement optical system 10 may be a known optical system. For example, in one alternative optical system, a ring-shaped measurement chart is projected to a fundus Ef from the periphery of a pupil, and then a fundus reflection light is extracted from the center portion of the pupil. Accordingly, a two-dimensional imaging device receives a ring-shaped fundus reflection image.

In addition to the measurement optical system 10 as described above, for example, the measurement optical system 10 may be a measurement optical system that includes: a projecting optical system for projecting a measurement light toward a fundus of an examinee's eye; and a light receiving optical system for receiving a reflection light obtained by reflection of the measurement light by the fundus with the use of a light receiving device. For example, an eye refractive power measurement optical system may include a Shack-Hartmann sensor. Alternatively, the measurement optical system 10 may be an apparatus employing another measurement method (e.g., apparatus employing phase difference method for projecting slit).

A dichroic mirror 29 is arranged between the objective lens 14 and the hole mirror 13. The dichroic mirror 29 guides a fixation chart light flux from a chart presenting optical system 30 to the eye E. The dichroic mirror 29 also guides a reflection light from an anterior segment of the eye E to an observation optical system 50. The dichroic mirror 29 transmits therethrough a light having a wavelength of the measurement light flux used for the measurement optical system 10.

The chart presenting optical system 30 (objective measurement optical system, subjective measurement optical system) is an optical system for presenting a chart to the examinee's eye. The chart presenting optical system 30 includes a visible light source 31 for chart presentation, a chart plate 32 having a fixation chart thereon, a light projecting lens 33, a half mirror 36, the dichroic mirror 29, and the objective lens 14.

The visible light source 31 serves as a fixation light source for fixating the examinee's eye. The chart presenting optical system 30 also functions as a refractive power correction optical system for correcting an eye refractive power of the examinee's eye with an astigmatism correcting optical system 60. The astigmatism correcting optical system 60 is arranged between the half mirror 36 and the light projecting lens 33.

The chart plate 32 is a rotatable disk plate and includes thereon a plurality of charts 32a. The plurality of charts 32a includes, for example, a fixation chart used for fogging the examinee's eye E at the time of objective measurement, a chart for visual acuity test at the time of subjective measurement, and a chart for glare test. The chart for visual acuity test is provided for each visual acuity value (e.g., 0.1, 0.3, . . . , 1.5).

The chart plate 32 is rotated by a motor 38. The plurality of charts 32a is arranged such that any one of the charts 32a to be arranged on an optical axis L2 of the chart presenting optical system 30 is switchable. A light flux from the chart 32a illuminated by the light source 31 travels toward the examinee's eye E through the optical members from the light projecting lens 33 to the dichroic mirror 29.

The light source 31 and the chart plate 32 (charts 32a) are integrally moved in a direction of the optical axis L2 by a drive mechanism 39 that includes a motor and a slide mechanism. At the time of objective measurement, the movement of the light source 31 and the chart 32a can fog the examinee's eye E. At the time of subjective measurement, the movement of the light source 31 and the chart 32 can optically change a distance (presenting distance) between a position of the chart being presented and the examinee's eye. Accordingly, such movement corrects a spherical refractive power of the examinee's eye. That is, the light projecting lens 33, the light source 31, and the chart 32a are moved, so that the chart presenting optical system 30 can correct a spherical dioptic power of the examinee's eye. The chart presenting optical system 30, therefore, functions as an optical system for spherical dioptic power correction.

The optical system for correcting the spherical dioptic power of a corrective lens may have a configuration in which a relay lens arranged in an optical path is moved in an optical axis direction.

The astigmatism correcting optical system (subjective measurement optical system) 60 includes two positive cylindrical lenses 61a and 61b that have substantially the same focal distance. The cylindrical lenses 61a and 61b are independently rotated around the optical axis L2 by rotation mechanisms 62a and 62b, respectively. The optical system for spherical dioptic power correction may have a configuration in which a corrective lens is moved into and out of an optical path of a chart presenting optical system.

Figure 2:
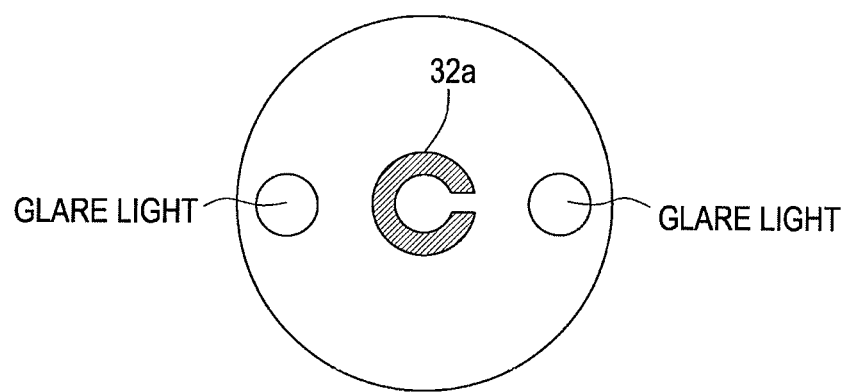
FIG. 2 is a diagram illustrating a visible light and a chart that are for glare test and are to be recognized visually and simultaneously by an examinee.

A glare test optical system (subjective measurement optical system) 80 includes a visible light source (glare light source) 81, and emits a glare light with respect to the eye E on which a chart is being presented. Herein, an amount of the light emitted from the light source is set such that the examinee feels the glare of the light emitted toward the eye thereof. The glare test optical system 80, for example, includes the visible light source 81 and a condenser lens 82. The visible light source 81 is used as a light source for glare test. The light flux emitted from the visible light source 81 travels toward the eye E through the condenser lens 82 and the half mirror 36. FIG. 2 illustrates a visible light and a chart for glare test, the visible light and the chart being to be recognized simultaneously and visually by an examinee. As illustrated in FIG. 2, the visible light (glare light) for glare test is formed in an outer circumferential vicinity of the chart 32a. In the embodiment, two light sources 81 are arranged so that the examiner can visually recognize the glare light as if recognizing a vehicle headlight.

A ring chart projecting optical system 45 and a working distance chart projecting optical system 46 are arranged toward the front of an anterior segment of the eye E. The ring chart projecting optical system 45 emits a near infrared light for projecting a ring chart to a cornea Ec of the eye E. The ring chart projecting optical systems 45 are symmetrically arranged with respect to an observation optical axis. The working distance chart projecting optical system 46 emits a near infrared light for projecting an infinity chart to the cornea Ec of the eye E, thereby detecting a state of an alignment of the apparatus along a working distance direction with respect to the examinee's eye. The working distance chart projecting optical systems 46 are symmetrically arranged with respect to a chart observation optical axis. The ring chart projecting optical system 45 can be used as an illumination for illuminating an anterior segment of the eye E and a chart for cornea shape measurement.

The observation optical system (imaging optical system) 50 shares the objective lens 14 and the dichroic mirror 29 with the chart presenting optical system 30. The observation optical system 50 includes a half mirror 35, an imaging lens 51, and a two-dimensional imaging device 52. The two-dimensional imaging device 52 includes an imaging surface that is positioned substantially in conjugation with the anterior segment of the examinee's eye. An output from the imaging device 52 is input into the control part 70, so that the anterior segment of the eye E is captured by the two-dimensional imaging device 52 and then displayed on a monitor 7. The observation optical system 50 also serves as an optical system for detecting an alignment chart image to be formed on a cornea of the eye E. The control part 70 detects a position of the alignment chart image.

The control part 70 is connected to the imaging device 22. The control part 70 calculates a refractive power based on an output from the imaging device 22. The control part 70 is connected to the imaging device 52, the drive mechanism 39, the motor 38, the light source 31, the light source 81, the rotation mechanisms 62a and 62b, a memory 75, the monitor 7, and an operation unit 90 to which the examiner performs various input operations. The operation unit 90 includes: a switch 90a for switching between an objective measurement mode and a subjective measurement mode; switches 90b and 90c for changing a visual acuity value of a chart to be presented; switches 90d and 90e for changing a spherical dioptic power of a corrective lens; and a switch 90f for inputting a mode selection signal for shifting to a glare test. The switch 90f is used to switch between a normal mode and a glare mode at the time of subjective measurement. The control part 70 controls the entire apparatus and calculates a value of the eye refractive power and a shape of the cornea, for example. The memory 75 stores therein the objective measurement mode and the subjective measurement mode. In the objective measurement mode, a ring image (ring reflection image) captured by the imaging device 22 is analyzed, thereby measuring the eye refractive power. In the subjective measurement mode, on the other hand, the eye refractive power is subjectively measured. The subjective measurement mode includes a normal mode used for visual acuity tests and a glare mode used for glare tests.

<Objective Measurement Mode>

Now, a description is given of a measurement operation of the apparatus including the above configuration. The apparatus is set into an objective measurement mode at the time of startup. The control part 70 controls the motor 38 to set a chart (fixation chart) for objective measurement in an optical path, the chart being used for fogging the eye E.

First, the examiner leads a face of the examinee to be securely placed on a face support unit (not shown), and then instructs the examinee to fixate a fixation chart. Subsequently, the examiner performs alignment of the apparatus with respect to the examinee's eye. The control part 70 allows the light source I1 to light based on a measurement start signal. The measurement light emitted from the measurement light source I1 is projected to the fundus Ef through the members from the relay lens 12 to the objective lens 14. Accordingly, the measurement light forms a spot-shaped point light source image that can rotate on the fundus Ef.

The light of the point light source image formed on the fundus Ef is reflected/scatted and is emitted from the eye E. The light is then condensed by the objective lens 14. The condensed light is re-condensed on an opening of the light receiving aperture 18 through the members from the dichroic mirror 29 to the total reflection mirror 17, so that the light is formed into a substantially parallel light flux by the collimator lens 19 (in the case of emmetropic eye). The substantially parallel light flux is extracted as a ring-shaped light flux by the ring lens 20, and the ring-shaped light flux is received as a ring image by the imaging device 22.

In such a measurement, a preliminary measurement of the eye refractive power is performed at the beginning. The visible light source 31 and the chart plate 32 are moved in an optical axis L2 direction based on a result of the preliminary measurement, thereby fogging the examinee's eye E. Then, the fogged examinee's eye undergoes an eye refractive power measurement.

Figure 3:
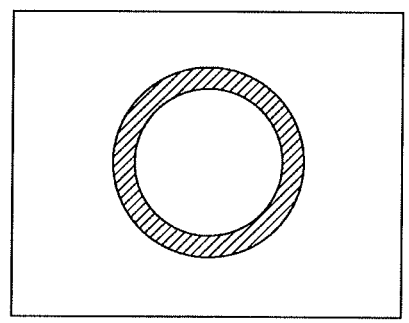
FIG. 3 is a diagram illustrating a ring image captured by an imaging device.

FIG. 3 illustrates a ring image captured by the imaging device 22 at the time of measurement. An output signal from the imaging device 22 is stored as image data (measurement image) in the memory 75. Then, the control part 70 specifies (detects) a position of the ring image in a plurality of meridian directions based on the measurement image stored in the memory 75. In this case, the control part 70 specifies a position of the ring image by detecting an edge thereof. For example, a reference for specifying the ring image position can be an intermediate point in a cut-off position in a waveform of a luminance signal that is cut off by a predetermined threshold value, a peak of a luminance signal waveform, or a gravity center of a luminance signal. Subsequently, the control part 70 determines an ellipse by approximation using a least-squares method based on the specified position of the ring image. The control part 70 then determines refractive errors in the plural meridian directions according to the ellipse determined by the approximation. Subsequently, the control part 70 calculates a value of the refractive power, a value S (spherical dioptic power), a value C (cylindrical dioptic power (astigmatism power)), and a value A (astigmatism axial angle) of the examinee's eye based on the refractive errors. The control part 70 allows the monitor 7 to display the calculation result (measurement result) thereon.

<Determination of Opacity>

A fundus reflection light which is obtained by reflection of a measurement light by a fundus is received by a light receiving device. The control part 70 determines the presence or absence of opacity in a light transmitting part of an examinee's eye based on a result of such light reception (light receiving signal). Herein, a description is given of an example of a measurement optical system that has a light receiving optical system for receiving a fundus reflection light as a two-dimensional pattern image with the use of a two-dimensional imaging device. In such an example, the control part 70 allows the light receiving device to receive the fundus reflection light, and then determines the presence or absence of opacity in a light transmitting part of the eye E based on a two-dimensional pattern received by the light receiving device. For example, the control part 70 stores the determination result in the memory 75, and uses such a result in a subjective measurement mode (described in detail later).

Figure 4A:
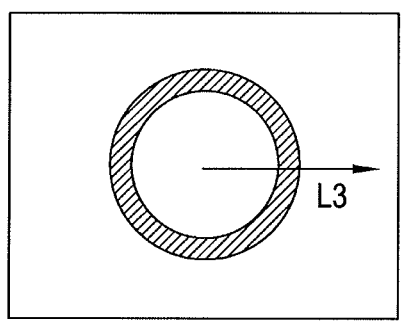
FIGS. 4A, 4B, and 4C are diagrams each illustrating the ring image captured by the imaging device and a luminance distribution of the ring image.
Figure 4A:
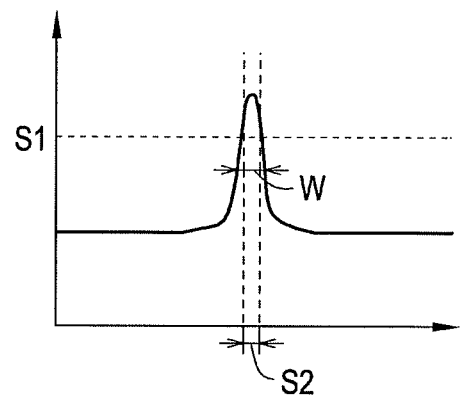
Figure 4B:
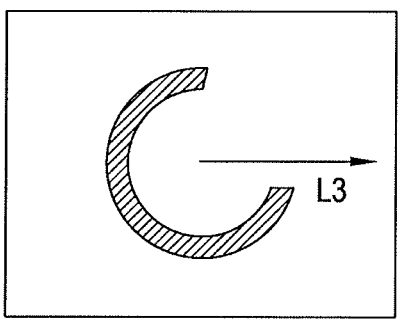
Figure 4B:
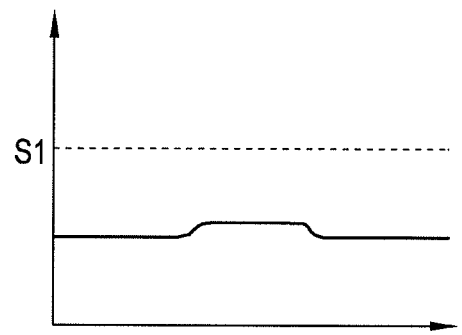
Figure 4C:
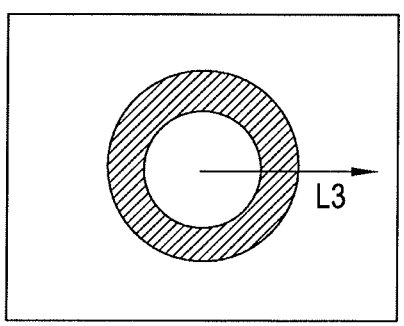
Figure 4C:
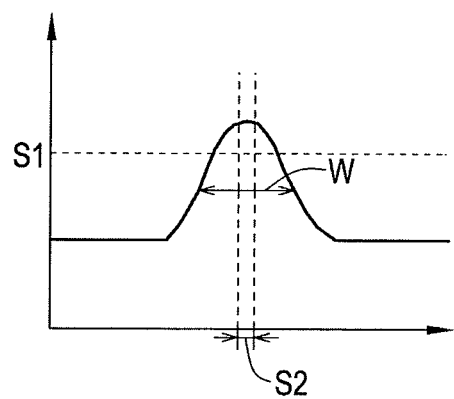

Now, opacity determination and control operation of the control part 70 are described. First, the control part 70 detects an edge of a ring image in a meridian direction for every one degree in a circumferential direction with reference to a center coordinate of the ring image. FIGS. 4A, 4B, and 4C illustrate luminance distributions (right diagrams) and corresponding ring images (left diagrams) captured by the imaging device 22. The luminance distribution is used to detect the edge of the ring image. The luminance distribution is obtained by detecting a luminance in a direction along a line L3 from the center of the ring image. FIG. 4A illustrates a ring image and a luminance distribution in a case where there is no opacity on the examinee's eye. Each of FIGS. 4B and 4C illustrates a ring image and a luminance distribution in a case where there is opacity on the examinee's eye. FIG. 4B illustrates the ring image having a missing area caused by the opacity, whereas FIG. 4C illustrates the ring image being blurred by the opacity.

As illustrated in FIG. 4A, when there is no opacity on the eye E, the ring image is formed (left diagram) without a missing area or being blurred. Then, upon obtaining a luminance distribution (right diagram) in the line L3 direction, a high luminance value corresponding to the edge of the ring image is obtained. The high luminance value is obtained substantially with respect to all the meridian directions. Moreover, a ratio of a half-value width W to a peak value in the luminance distribution becomes small (that is, half-value width W becomes relatively narrow). The half-value width W becomes narrow with respect to substantially all the meridian directions.

When there is opacity on the eye E due to a lesion such as cataract, a missing area is generated on a ring image or a ring image is blurred. For example, a ring image having a missing area is formed as illustrated in FIG. 4B (left diagram). In such a case, a sharp peak is not generated (luminance hardly increases) in a line L3 direction in a luminance distribution (right diagram). In the luminance distribution for the missing area, therefore, the luminance hardly increases.

Moreover, as illustrated in FIG. 4C, there are cases where a blurred ring image is formed (left diagram). When the blurriness is being generated, obtainment of the luminance distribution (right diagram) in a line L3 direction lowers a luminance value relative to a case where there is no opacity. In the luminance distribution for the blurred region, therefore, a peak is lower than a case where there is no opacity. In addition, a half-value width W is wider. Accordingly, a peak having the wider half-value width W is provided in the luminance distribution for the blurred region.

The reason for generating the missing area on the ring image is the presence of severe opacity on an eye corresponding to the missing area, the severe opacity being caused by cataract on the examinee's eye. This opacity portion blocks almost all the measurement light flux to be transmitted through the examinee's eye, causing difficulty in condensing the light flux into the imaging device 22 for this area.

Moreover, the reason for generating the blurriness on the ring image is the presence of severe opacity on an eye corresponding to this area, the severe opacity being caused by cataract on the examinee's eye. In such a case, the opacity portion scatters the measurement light flux to be transmitted through the eye. Accordingly, when the measurement light flux reaches the imaging device 22, a widened ring image is formed.

Therefore, in the determination below, these characteristics are utilized to set a threshold value S1 to distinguish between a peak value provided when there is severe opacity and a peak value provided when there is no opacity. The control part 70 determines the presence or absence of opacity in the area along each meridian direction based on whether or not a peak value in a luminance distribution exceeds the threshold value S1. In addition, a threshold value S2 is set to distinguish between a half-value width provided when there is opacity and a half-value width provided when there is no opacity. The control part 70 determines the presence or absence of opacity in the area along each meridian direction based on whether or not a half-value width in a luminance distribution exceeds the threshold value S2. The control part 70 also evaluates the opacity on the entire examinee's eye based on the presence or absence of opacity in the area along each meridian direction.

After determining the presence or absence of opacity, the control part 70 stores the determination results in the memory 75 at the measurement completion in the objective measurement mode.

<Subjective Measurement Mode>

Upon completion of the objective measurement, the control part 70 switches a measurement mode to a subjective measurement mode when the subjective measurement mode in the switch 90a is selected for a subjective test.

The subjective measurement mode includes a normal mode used for visual acuity test on an eye in a subjective manner, and a glare mode used for glare test. The normal mode is selected at the time of mode switching.

<Normal Mode>

Upon switching to the subjective measurement mode, a test is performed in the normal mode at first. The normal mode of the subjective measurement mode is described as follows. Upon switching to the subjective measurement mode, the control part 70 changes a state of a refractive power correction optical system based on the refractive dioptic powers (spherical dioptic power S, astigmatic dioptic power C, and astigmatism axial angle A) of the examinee's eye, the refractive dioptic powers being obtained by the objective measurement. That is, the control part 70 changes arrangements of the chart presenting optical system 30 and the astigmatism correcting optical system 60 and selects a chart such that the examinee can easily see the chart. Accordingly, the examinee can see the chart in a state that the visual acuity (refractive power error) is being corrected. That is, the control part 70 moves the visible light source 31 and the chart plate 32 in the optical axis L2 direction based on the spherical dioptic power S, thereby obtaining a state that the examinee has the corrected refractive power error of the spherical dioptic power (spherical refractive power) S. Moreover, the control part 70 drives the astigmatism correcting optical system 60 based on the astigmatic dioptic power C and the astigmatism axial angle A, thereby correcting the astigmatic refractive error (in corrected state).

Moreover, the control part 70 switches charts for visual acuity on the chart plate 32 based on a corrected visual acuity value that has been presumed at the time of objective measurement. For example, when a corrected visual acuity of an examinee's eye is presumed to 0.5, the control part 70 controls the motor 38 to rotate the chart plate 32. Accordingly, the control part 70 allows the visual acuity test chart corresponding to the visual acuity value 0.5 to be arranged on the optical axis L2 as an initial presentation chart for a subjective test.

After presenting the initial presentation chart to the examinee's eye, the examiner performs the visual acuity test on the eye. The examiner asks the examinee what the type of chart is. The examiner operates the switch 90b or 90c depending on the response from the examinee to switch the chart to be presented. When the response from the examinee is correct, the examiner selects the switch 90b to switch the chart for a chart corresponding to the visual acuity value that is one level higher. When the response from the examinee is not correct, on the other hand, the examiner selects the switch 90c to switch the chart for a chart corresponding to the visual acuity value that is one level lower. Such procedures are repeated to obtain the smallest chart that can be read by the examinee (best visual acuity of examinee).

After obtaining the best visual acuity value, the examiner checks the most positive spherical dioptic power that can obtain the best visual acuity value. That is, the operation of the switch 90d or 90e by the examiner can change a correction amount of the spherical dioptic power S. Selection of the switch 90d or 90e moves the visible light source 31 and the chart plate 32 in the optical axis L2 direction, so that the correction amount of the spherical dioptic power is changed, thereby determining the spherical dioptic power S which can obtain the best visual acuity and has the most positive value. Accordingly, a reference value for prescription of eyeglass lenses or contact lenses can be obtained.

<Glare Mode>

Upon completion of measurement in the normal mode of the subjective measurement mode, a measurement end signal is input into the control part 70. Then, the control part 70 determines whether or not to prompt the examiner to switch the mode based on the determination result stored in the memory 75, the determination result including the presence or absence of opacity.

When the determination result in the memory 75 indicates the presence of opacity, the control part 70 prompts the examiner to execute the glare test by using the glare test optical system 80. That is, the control part 70 allows an external unit to display thereon the necessity for glare test. For example, the control part 70 allows the monitor (display unit) 7 to display thereon a message for the examiner to switch the mode. That is, the control part 70 allows the monitor 7 to display thereon a message indicating that the measurement mode should be changed from the normal mode to the glare mode.

When the examiner selects the switch 90f for switching to the glare mode, the control part 70 switches the measurement mode from the normal mode to the glare mode.

In the glare mode, a glare test is performed. In the glare test, for example, the chart 32a (e.g., Landolt ring, striped pattern) is presented to a center portion of a visual field of the examinee. In addition, a glare light is applied toward the examinee's eye. The glare light is applied such that the examinee can visually recognize that glare light is formed in spots in specific positions in the periphery of the chart 32a. Alternatively, the glare light may be applied such that the examinee can visually recognize that the glare light is formed to surround the periphery of the chart 32a.

Then, the examinee responds whether or not the chart 32a presented by the chart presenting optical system 30 is visually recognizable while the eye of the examinee is being irradiated with the glare light.

Now, the glare mode is described. When the measurement mode is switched to the glare mode, the control part 70 allows the light source 81 to light. The glare light emitted from the light source 81 is projected to the fundus Ef through the members from the condenser lens 82 to the objective lens 14.

The examinee looks at the chart 32a in a state that the glare light illuminates as it were headlights of a vehicle (bright state), and then responds whether the chart 32a is recognizable. The examiner can know whether or not the examinee's eye E has cataract based on the response of the examinee.

When the examinee's eye has cataract, the chart 32a is not visible or less visible by the glare light due to visual acuity reduction associated with scattering of the glare light by opaque crystalline lens. When the examinee's eye does not have cataract, on the other hand, the glare light is not scattered by crystalline lens. Thus, the chart 32a can be visible. Accordingly, the presence or absence of cataract can be subjectively recognized.

In the embodiment, for example, the smallest chart that can be read by the examinee (best visual acuity of examinee) is obtained by switching the charts while the glare light is being applied as similar to the visual acuity test in the normal mode. The examiner compares the obtained best visual acuity and the best visual acuity in the normal mode, and determines the presence or absence of visual acuity reduction caused by the presence or absence of glare light.

In the glare test according to the embodiment, the comparison is made between the best visual acuity provided when there is glare light and the best visual acuity provided when there is not glare light. However, the glare test is not limited thereto as long as the examiner can determine whether or not there is any influence on chart visibility by glare light. For example, a certain chart is presented to an examinee, and then the examiner asks whether or not the presence or absence of glare light makes visibility of the chart different. The examiner can determine the presence or absence of cataract based on the response of the examinee.

According to the apparatus, therefore, a refractive power of the examinee's eye can be tested objectively or subjectively. Moreover, the presence or absence of cataract can be tested objectively or subjectively, thereby improving a screening accuracy and shortening a test time. Moreover, such test results can be used for determination of the presence or absence of cataract surgery indication, determination of timing for the surgery, determination of recovery of visual function after the surgery, and a visual function test in a vitreoretinal surgery or treatment for macular disease, for example. According to the apparatus, therefore, eye dysfunctions such as cataract can be diagnosed simply and quickly.

According to the embodiment, two glare light sources 81 are employed. Alternatively, one glare light source 81 may be employed. Alternatively, three or more glare light sources 81 may be employed. In such a case, the glare light sources 81 are provided such that the chart 32a is surround by the glare light. That is, the apparatus may have any configuration as long as the presence or absence of the influence of glare light on visual acuity of an examinee can be determined.

In the embodiment, the control part 70 allows the monitor 7 to display thereon the message to prompt the examiner to switch the mode to the glare mode. However, the embodiment is not limited thereto. For example, the control part 70 may shift to a glare test based on the determination result stored in the memory 75 without considering the intension of the examiner, the determination result including the presence or absence of opacity. In such a case, when the determination result indicating the presence of opacity is stored in the memory 75, the control part 70 switches the measurement mode from a normal mode to a glare mode.

According to the embodiment, the light source 81 for glare test is disposed on the optical path that differs from that of the chart presenting optical system 30. However, the embodiment is not limited thereto. For example, the light source 81 for glare test may be disposed on the optical path of the chart presenting optical system 30. For example, the light source 81 for glare test may be disposed on an outer side of the chart plate 32 or an outer side of the ring chart projecting optical system 45 or the working distance chart projecting optical system 46. Moreover, the light source 81 for glare test may be disposed in front of the chart plate 32. The light source 81 for glare test may be disposed at any position as long as an examinee can see the glare light.

In the embodiment, the examiner selects the switch 90a to switch the measurement mode from the objective measurement mode to the subjective measurement mode. Alternatively, the control part 70 may switch the measurement mode to the subjective measurement mode upon completion of objective measurement.

In the embodiment, when the presence of opacity is determined at the time of objective measurement, in the subjective measurement mode, the control part 70 prompts the examiner to execute the glare mode subsequent to the normal mode. However, the embodiment is not limited thereto. For example, when the presence of opacity is determined at the time of objective measurement, in the subjective measurement mode, the control part 70 may switch the measurement mode from the normal mode to the glare mode to continue the measurement.

Alternatively, the control part 70 may execute the measurement in the glare mode subsequent to the measurement in the normal mode, and then execute the objective measurement.

Also, the control part 70 may obtain a ring image prior to and subsequent to the subjective measurement when switching the measurement mode from the normal mode to the glare mode. The control part 70 may determine whether or not to execute the glare mode based on a result of analysis of the ring image captured by the imaging device 22. That is, the control part 70 may not need to store the presence or absence of opacity in the memory 75 at the time of objective measurement. The control part 70 can obtain and analyze a ring image before switching the measurement mode to the glare mode.

Moreover, when the presence of opacity is determined at the time of objective measurement, the control part 70 may execute a glare test without measurement in the normal mode (or may prompt examiner to execute glare mode). In addition, the apparatus may be configured such that an examiner can arbitrarily set a type of measurement modes to be executed and/or execution sequence of measurement modes.

In the embodiment, the control part 70 uses the ring image at the time of objective measurement. However, the embodiment is not limited thereto as long as, for example, the control part 70 determines the presence or absence of opacity in a light transmitting part of the examinee's eye based on a result of reception of fundus reflection light which is obtained by reflecting the light projected to fundus by the fundus.

For example, the control part 70 may obtain a retro-illumination image of an anterior segment (anterior segment image), and determine the presence or absence of opacity based on the obtained retro-illumination image. In such a case, the control part 70 allows the inside of a pupil to be illuminated with a fundus reflection light which is obtained by projecting light flux to the fundus, thereby obtaining the retro-illumination image. For example, the projecting optical system 10a is used as an optical system for projecting the light flux. The observation optical system 50 may be used as an optical system for forming the retro-illumination image. When the presence or absence of opacity is determined, the control part 70 may calculate an area of a shielding portion inside the pupil (portion having low light quantity level) by performing image processing. In such a case, the control part 70 determines the presence or absence of opacity based on whether the calculated area is within an acceptable range.

In addition, the method for determining the presence or absence of opacity based on the light reception result can include an indirect determination method. For example, the presence of opacity may be determined when a measurement error is output or measurement reliability (e.g., amount of shift between actual position of ring image and approximated position of ellipse) is low.

Moreover, the eye measurement apparatus according to the embodiment may be expressed as first to tenth eye refractive power measurement apparatuses as follows.

The first eye refractive power measurement apparatus includes: a measurement optical system which objectively measures an eye refractive power of an examinee's eye, and has a light projecting optical system for projecting a measurement light toward a fundus of the examinee's eye and a light receiving optical system for receiving a reflection light obtained by reflection of the measurement light by the fundus with the use of a light receiving device; a chart presenting optical system for presenting a chart to the examinee's eye; a glare test optical system which includes a glare light source and emits a glare light with respect to the examinee's eye to which the chart is presented; and a guide unit (control part) which determines the presence or absence of opacity in a light transmitting part of the examinee's eye based on a light receiving signal corresponding to a reflection light obtained by reflecting a light projected to the fundus by the fundus, and guides an examiner to execute a glare test using the glare test optical system when the presence of opacity is determined.

In the second eye refractive power measurement apparatus according to the first eye refractive power measurement apparatus, the guide unit allows the light receiving device to receive the reflection light which is reflection of the measurement light by the fundus and determines the presence or absence of opacity in a light transmitting part of the examinee's eye based on the light receiving signal from the light receiving device.

The third eye refractive power measurement apparatus according to the first eye refractive power measurement apparatus includes an input mechanism for inputting a mode switching signal to shift to the glare test and a display mechanism, and the guide unit allows the display mechanism to display thereon a message for guiding the examiner to operate the input mechanism when the presence of opacity is determined.

In the fourth eye refractive power measurement apparatus according to the first eye refractive power measurement apparatus, the guide unit executes a glare test using the glare test optical system when the presence of opacity is determined.

In the fifth eye refractive power measurement apparatus according to the first eye refractive power measurement apparatus, the guide unit guides the examiner to execute a glare test subsequent to a subjective refractive power measurement when the presence of opacity is determined.

In the sixth eye refractive power measurement apparatus according to the first eye refractive power measurement apparatus, the guide unit guides the examiner to execute a glare test subsequent to an objective refractive power measurement performed using the measurement optical system when the presence of opacity is determined.

In the seventh eye refractive power measurement apparatus according to the first eye refractive power measurement apparatus, the guide unit determines the presence or absence of opacity in a light transmitting part of the examinee's eye based on at least whether or not a luminance of the light receiving signal exceeds a predetermined threshold value or whether or not a half-value width of the light receiving signal exceeds a predetermined threshold value.

In the eighth eye refractive power measurement apparatus according to the second eye refractive power measurement apparatus, the light receiving optical system receives a ring reflection image obtained by reflection of the measurement light by the fundus with the use of a two-dimensional light receiving device, whereas the guide unit determines the presence or absence of opacity by processing the ring reflection image received by the two-dimensional light receiving device.

In the ninth eye refractive power measurement apparatus according to the first eye refractive power measurement apparatus, the guide unit includes an optical system for capturing a retro-illumination image of an anterior segment which is obtained by reflecting a light projected to the fundus by the fundus, and determines the presence or absence of opacity in a light transmitting part of the examinee's eye by processing the captured retro-illumination image.

In the tenth eye refractive power measurement apparatus according to the first eye refractive power measurement apparatus, the guide unit includes: a determination unit for determining the presence or absence of opacity in a light transmitting part of the examinee's eye based on a light receiving signal corresponding to a reflection light obtained by reflecting the light projected to the fundus by the fundus; and a prompt unit for prompting the examiner to execute a glare test using the glare test optical system when the presence of opacity is determined by the determination unit.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An eye refractive power measurement apparatus comprising:
    a subjective measurement optical system configured to subjectively measure an examinee's eye, the subjective measurement optical system including:
      a chart to be presented to the examinee's eye; and
      a glare light source for irradiating the examinee's eye with a glare light;
    an objective measurement optical system to objectively measure an eye refractive power of the examinee's eye, the objective measurement optical system including:
      a light projecting optical system for projecting a measurement light toward a fundus of the examinee's eye; and
      a light receiving optical system including a light receiving device for receiving a fundus reflection light obtained by reflecting the measurement light by the fundus; and
    a control part configured to determine presence or absence of opacity in a light transmitting part of the examinee's eye based on a light receiving signal obtained by the fundus reflection light and, when the presence of opacity is determined, to allow display of necessity for a glare test which is a subjective measurement to be performed in a state that the examinee's eye is irradiated with the glare light.

2. The eye refractive power measurement apparatus according to claim 1, further comprising an input unit for receiving a glare test execution instruction,
    wherein the control part controls the subjective measurement optical system in response to an input of the instruction to execute the glare test.

3. The eye refractive power measurement apparatus according to claim 1, further comprising a display unit for displaying a message thereon,
    wherein when the presence of opacity is determined, the control part allows the display unit to display thereon a message indicating the necessity for the glare test.

4. The eye refractive power measurement apparatus according to claim 1,
    wherein when the presence of opacity is determined, the control part allows display of necessity for the glare test after execution of the subjective measurement in a state that the examinee's eye is not irradiated with the glare light.

5. The eye refractive power measurement apparatus according to claim 1, further comprising an imaging optical system for capturing a retro-illumination image of an anterior segment of the examinee's eye,
    wherein the control part determines the presence or absence of opacity in the light transmitting part of the examinee's eye by processing the captured retro-illumination image.

6. The eye refractive power measurement apparatus according to claim 1,
    wherein when the presence of opacity is determined, the control part allows display of necessity for the glare test after executing the objective measurement.

7. The eye refractive power measurement apparatus according to claim 1,
    wherein the control part determines the presence or absence of opacity in the light transmitting part of the examinee's eye based on at least whether or not a luminance of the light receiving signal exceeds a predetermined threshold value or whether or not a half-value width of the light receiving signal exceeds a predetermined threshold value.

8. The eye refractive power measurement apparatus according to claim 1,
    wherein the light receiving optical system receives a ring-shaped fundus reflection light with use of a two-dimensional light receiving device, and
    the control part determines the presence or absence of opacity in the light transmitting part of the examinee's eye by processing a ring-shaped image received by the two-dimensional light receiving device.

9. An eye refractive power measurement apparatus comprising:
    a subjective measurement optical system configured to subjectively measure an examinee's eye, the subjective measurement optical system including:
      a chart to be presented to the examinee's eye; and
      a glare light source for irradiating the examinee's eye with a glare light;
    an objective measurement optical system to objectively measure an eye refractive power of the examinee's eye, the objective measurement optical system including:
      a light projecting optical system for projecting a measurement light toward a fundus of the examinee's eye; and a light receiving optical system including a light receiving device for receiving a fundus reflection light obtained by reflecting the measurement light by the fundus; and a control part configured to determine presence or absence of opacity in a light transmitting part of the examinee's eye based on a light receiving signal obtained by the fundus reflection light and, when the presence of opacity is determined, to control the subjective measurement optical system to execute a glare test which is a subjective measurement to be performed in a state that the examinee's eye is irradiated with the glare light.

10. The eye refractive power measurement apparatus according to claim 9,
wherein when the presence of opacity is determined, the control part executes the glare test after execution of the subjective measurement in a state that the examinee's eye is not irradiated with the glare light.

11. The eye refractive power measurement apparatus according to claim 9, further comprising an imaging optical system for capturing a retro-illumination image of an anterior segment of the examinee's eye,
wherein the control part determines the presence or absence of opacity in the light transmitting part of the examinee's eye by processing the captured retro-illumination image.

12. The eye refractive power measurement apparatus according to claim 9, further comprising an input unit for receiving a glare test execution instruction,
wherein the control part controls the subjective measurement optical system in response to an input of the instruction to execute the glare test.

13. The eye refractive power measurement apparatus according to claim 12, further comprising a display unit for displaying a message thereon,
wherein when the presence of opacity is determined, the control part allows the display unit to display thereon a message indicating necessity for the glare test.

14. The eye refractive power measurement apparatus according to claim 9,
wherein when the presence of opacity is determined, the control part executes the glare test after executing the objective measurement.

15. The eye refractive power measurement apparatus according to claim 9,
wherein the control part determines the presence or absence of opacity in the light transmitting part of the examinee's eye based on at least whether or not a luminance of the light receiving signal exceeds a predetermined threshold value or whether or not a half-value width of the light receiving signal exceeds a predetermined threshold value.

16. The eye refractive power measurement apparatus according to claim 9,
wherein the light receiving optical system receives a ring-shaped fundus reflection light with use of a two-dimensional light receiving device, and
the control part determines the presence or absence of opacity in the light transmitting part of the examinee's eye by processing a ring-shaped image received by the two-dimensional light receiving device.

17. An eye measurement apparatus comprising:
a subjective measurement optical system configured to subjectively measure an examinee's eye, the subjective measurement optical system including:
a chart to be presented to the examinee's eye; and
a glare light source for irradiating the examinee's eye with a glare light;
a control part configured to determine presence or absence of opacity in a light transmitting part of the examinee's eye; and
a memory unit comprising the determination result indicating the presence or absence of opacity, wherein
when the memory comprises the determination result indicating the presence of opacity, the control part controls the subjective measurement optical system to execute a glare test which is a subjective measurement to be performed in a state that the examinee's eye is irradiated with the glare light.

18. The eye refractive power measurement apparatus according to claim 1,
wherein the eye refractive power measurement apparatus further comprises a switch for switching a measurement mode of the apparatus to the glare test, and
when the control part determines the presence of opacity, the control part displays on a monitor a message to prompt a user of the apparatus to switch the measurement mode to the glare test.

19. The eye refractive power measurement apparatus according to claim 9,
wherein the eye refractive power measurement apparatus further comprises a switch for switching a measurement mode of the apparatus to the glare test, and
when the control part determines the presence of opacity, the control part displays on a monitor a message to prompt a user of the apparatus to switch the measurement mode to the glare test.

* * * * *